(12) United States Patent
Trabelsi et al.

(10) Patent No.: US 6,691,563 B1
(45) Date of Patent: Feb. 17, 2004

(54) UNIVERSAL DIELECTRIC CALIBRATION METHOD AND APPARATUS FOR MOISTURE CONTENT DETERMINATION IN PARTICULATE AND GRANULAR MATERIALS

(75) Inventors: Samir Trabelsi, Athens, GA (US); Stuart O. Nelson, Athens, GA (US); Andrzej W. Kraszewski, Athens, GA (US)

(73) Assignee: The United States of America as represented by the Department of Agriculture, Washington, DC (US)

( * ) Notice: Subject to any disclaimer, the term of this patent is extended or adjusted under 35 U.S.C. 154(b) by 0 days.

(21) Appl. No.: 09/829,966

(22) Filed: Apr. 11, 2001

Related U.S. Application Data

(60) Provisional application No. 60/196,093, filed on Apr. 11, 2000.

(51) Int. Cl.[7] ............................ G01N 25/56; G01R 27/02
(52) U.S. Cl. ................................. 73/73; 324/640
(58) Field of Search ............................... 73/73, 74, 75, 73/76; 324/633, 637, 634, 640

(56) References Cited

U.S. PATENT DOCUMENTS

| | | | |
|---|---|---|---|
| 4,361,801 A | 11/1982 | Meyer et al. | 324/58.5 R |
| 5,039,947 A | 8/1991 | Kraszewski et al. | 324/634 |
| 5,666,061 A | 9/1997 | Assenheim | 324/636 |
| 5,934,997 A | 8/1999 | Nelson et al. | 460/7 |
| 5,939,888 A | 8/1999 | Nelson | 324/640 |
| 6,147,503 A | 11/2000 | Nelson et al. | 324/637 |

OTHER PUBLICATIONS

Meyer, W., et al., "Feasibility Study of Density–Independent Moisture Measurement with Microwaves", *IEEE Transactions on Microwave Theory and Techniques*, vol. MTT–29(7), pp. 732–739, Jul. 1981.

Menke, F., et al., "New Density–Independent Moisture Measurement Methods Using Frequency–Swept Microwave Transmission", *IEEE MTT–S Digest*, vol. TH2C–7, pp. 1415–1418, 1996.

Kraszewski, A., et al., "Preliminary Study on Microwave Monitoring of Moisture content in Wheat", *Journal of Microwave Power*, vol. 12(3), pp. 241–252, 1977.

Trabelsi, S., et al., "Simultaneous Determination of Density and Water Content of Particulate Materials by Microwave Sensors", *Electronics Letters*, vol. 33(10), pp. 874–876, May 8, 1997.

Kraszewski, A.W., et al., "Nondestructive Microwave Measurement of Moisture Content and Mass of Single Peanut Kernels", *Transactions of the ASAE*, vol. 36(1), pp. 127–134, Jan.–Feb., 1993.

Kraszewski, A.W., et al., "Microwave Resonator Technique for Moisture Content Determination in Single Soybean Seeds", *IEEE Transactions on Instrumentation and Measurement*, vol. 38(1), pp. 79–84, Feb., 1989.

Kraszewski, A.W., et al., "Moisture Content Determination in Single Corn Kernels by Microwave Resonator Techniques", *Journal Agric. Engng. Res.*, vol. 48, pp. 77–87, 1991.

(List continued on next page.)

*Primary Examiner*—Hezron Williams
*Assistant Examiner*—David A. Rogers
(74) *Attorney, Agent, or Firm*—John D. Fado; Gail E. Poulos

(57) ABSTRACT

A universal calibration method and apparatus for nondestructive real time determination of moisture content in particulate or granular materials by radio-frequency sensors is described which is bulk-density and material-independent and remains valid across instruments of different designs.

4 Claims, 11 Drawing Sheets

OTHER PUBLICATIONS

McLendon, B.D., et al., "Density–Independent Microwave Measurement of Moisture Content in Static and Flowing Grain", *American Society of Agricultural Engineers*, vol. 36(3), pp. 827–835, May–Jun., 1993.

Trabelsi, S., et al., "Universal Microwave Moisture Sensor for Granular Materials", *ASAE Annual International Meeting 2000*, Paper No. 003061.

Trabelsi, S., et al., "A Unified Calibration Method for Moisture Sensing in Particulate Materials", Reprinted from the Collection of Papers at the Third Workshop on Electromagnetic Wave Interaction with Water and Moist Substances, Athens, GA, Apr. 11–13, 1999, pp. 178–183.

Kraszewski, A.W., et al., "Determination of Moisture Content and Bulk Density of Shelled corn by Measurement of Microwave Parameters", *J. Agric. Engng. Res.*, vol. 58, pp. 37–46, 1994.

Kent, M., et al., "Microwave Moisture and Density Measurements in Particulate Solids", *Trans. Inst. M.C.*, 8(3), pp. 161–168, Jul.–Sep. 1986.

Trabelsi, S. et al., "Density–and Structure–Independent Calibration Method for Microwave Moisture Determination in Granular Methods", *IEEE Antennas and Propagation Society International Symposium Digest*, vol. 3, pp. 1958–1961, 1999.

Kraszewski, A.W., et al., "Moisture Content Determination In Single Peanut Kernels with a Microwave Resonator", *Peanut Sciences*, vol. 20, pp. 27–31, 1993.

Trabelsi, S., et al., "Dielectric Calibration Methods for Industrial Microwave Sensors", *Second World Congress on Microwave & Radio Frequency Processing (Meeting Guide MWP–DP– 07)*, Apr. 2–6, 2000.

Nelson, S.O., et al., "Advances in Sensing Grain Moisture Content by Microwave Measurements", *Transactions of the ASAE*, vol. 41(2), pp. 483–487, 1998.

Trabelsi, S., et al., "Nondestructive Microwave Characterization for Determining the Bulk Density and Moisture Content of Shelled Corn", *Meas. Sci. Technol.*, vol. 9, pp. 1548–1556, 1998.

Kraszewski, A.W., et al., "Wheat Permittivity Measurements in Free Space", *International Microwave Power Institute*, vol. 31(3), pp. 135–141, 1996.

Trabelsi, S., et al., "Microwave Dielectric Properties of Shelled, Yellow–Dent Field Corn", *J. Microwave Power and Electromagnetic Energy*, vol. 32(3), pp. 188–194, 1997.

Trabelsi, S., et al., "Density–Independent Functions for On–Line Microwave Moisture Meters: A General Discussion", *Meas. Sci Technol.*, vol. 9, pp. 570–578, 1998.

Kraszewski, A.W., et al., "Density–Independent Moisture Determination in Wheat by Microwave Measurement", approved for publication by *Food and Process Engineering Inst. of ASAE* In Feb. 1991, pp. 1–8.

Kraszewski, A.W., et al., "Comparison of Density–Independent Expressions for Moisture Content Determination in Wheat at Microwave Frequencies", *J. Agric. Engng. Res.*, vol. 71, pp. 227–237, Article No. ag980320, 1998.

Nelson, S.O., et al., "Grain Moisture Content Determination by Microwave Measurements", *Transactions of the ASAE*, vol. 33(4), pp. 1303–1307, Jul.–Aug., 1990.

Kraszewski, A.W., et al., "Simple Grain Moisture Content Determination from Microwave Measurements", *Transactions of the ASAE*, vol. 41(1), pp. 129–134, 1998.

Nelson, S.O., "Non–Destructive Radio–Frequency and Microwave Measurement of Moisture Content in Agricultural Commodities", *Postharvest News and Information*, vol. 5(1), pp. 7N–10N, 1994.

Nelson, S.O., et al., "Advances in Sensing Grain Moisture Content by Microwave Measurements", *Transactions of the ASAE*, vol. 41(2), pp. 483–487, 1998.

Kupfer, K., "Possibilities and Limitations of Density–Independent Moisture Measurements with Microwaves", *School of Architecture and Building*, Weimar, Germany, Chapter 21, pp. 313–327.

Trabelsi, S., et al., "New Density–Independent Calibration Function for Microwave Sensing of Moisture Content in Particulate Materials", *IEEE Transactions on Instrumentation and Measurement*, vol. 47(3), pp. 613–622, Jun. 1998.

UNIVERSAL DIELECTRIC CALIBRATION METHOD AND APPARATUS FOR MOISTURE CONTENT DETERMINATION IN PARTICULATE AND GRANULAR MATERIALS

CROSS REFERENCE TO PROVISIONAL APPLICATION

This application claims benefit of provisional application Serial No. 60/196,093, filed Apr.11, 2000.

BACKGROUND OF THE INVENTION

1. Field of Invention

The present invention relates to a universal method and apparatus for the determination of moisture content of material, manufactured or natural, such as cereal grain and seed, for example, from radio-frequency measurement of their dielectric properties independent of bulk density changes, structure (shape, dimensions, and surface characteristics), and composition of the material using a universal calibration algorithm that remains valid across instruments of different designs.

2. Description of the Related Art

Moisture content of natural or manufactured particulate and granular materials is crucial in many industries including mining, construction, pharmaceutical, food and agriculture. It is commonly used as a quality control factor and/or an indicator for the optimization of a given process. Methods for moisture content determination in natural and manufactured materials can be classified into two categories: direct methods and indirect methods. Direct methods rely on weight loss (oven drying method) or chemical titration (Karl-Fisher). Direct methods require off-line testing of a few samples. They are accurate and are usually used as references for the calibration of other methods. The major disadvantages are their destructive nature and the time they require. Therefore, they do not meet the needs of highly automated industries for which moisture content has to be determined in real time for large quantities of material. Indirect methods are based on the measurement of a property of the material that is directly correlated with moisture content. Nuclear radiation-, infrared- and dielectric-based sensors are the most commonly used indirect measurement techniques. They have the advantage of being nondestructive, contactless and, most importantly, provide a tool for on-line continuous measurement of moisture content. Moreover, with better sampling and averaging over the entire material volume, they give a better estimate of the true moisture content.

Nuclear radiation-based sensors are expensive and present potential hazards. Infrared sensors provide mainly surface moisture content. Dielectric-based methods are increasingly used for the development of cost-effective reliable moisture sensors which can be mounted on-line and provide in real time moisture content representative of the whole volume of material (Nyfors and Vainikainen, Industrial Microwave Sensors, Artech House, 1989; Kraszewski, Ed., Microwave Aquametry—Electromagnetic Interaction with Water-Containing Materials, New York: IEEE Press, 1996; Baltes et al., Eds., Sensors Update, Volume 7, Wiley-VCH, 2000, Trabelsi et al., Electronics Letters, Volume 33 (10), 874–876, 1997; Trabelsi et al., Trans. ASAE, Volume 42 (2), 531–536, 1999). The dielectric properties of a given material are intrinsic properties represented by the relative complex permittivity which is a complex number, often written as $\varepsilon = \varepsilon' - j\varepsilon''$. The real part, $\varepsilon'$, reflects the ability of a material to store electric-field energy, and the imaginary part, $\varepsilon''$, is usually associated with the ability of a material to dissipate electric energy in the form of heat. $j = \sqrt{-1}$ is the imaginary unit. During the past few years a trend for using higher and higher frequencies developed with a shift from the frequency range $10^6$ Hz–$10^8$ Hz to the frequency range $10^9$ Hz–$10^{11}$ Hz. The essence of microwave moisture sensing is based on the polar nature of the water molecules, which translates into a high correlation between the dielectric properties of moist substances and their moisture content (Hasted, Aqueous dielectrics, London: Chapman and Hall, 1973), the absence of ionic conductivity, and the spatial resolution of the electromagnetic waves, providing information relating to the whole volume of the material rather than limited to the surface of the material. For most wet dielectric materials (Hasted, Aqueous dielectrics, London: Chapman and Hall, 1973), both $\varepsilon'$ and $\varepsilon''$ are dependent on the wave frequency, temperature of the material, its water content, and to some extent its composition. For particulate and granular materials, they also depend on packing properties that produce bulk density variations (Nelson, Cereal Chem., Volume 58 (6), 487–492, 1981; J. Microwave Power, Volume 18 (2), 143–153, 1983). At a given frequency, temperature and bulk density have effects similar to that of moisture content on the dielectric properties; both $\varepsilon'$ and $\varepsilon''$ increase linearly with temperature, moisture content, and bulk density. Therefore, development of microwave moisture sensors based on the principle of dielectric properties measurements requires that effects related to variables other than moisture content be accounted for or eliminated by using calibration techniques that are not sensitive to those variables.

The compensation/correction approach implies combination and integration of several different sensing devices, such as sensors for bulk density and temperature, which always increase the overall cost and complicates the calibration procedures. Also, the multiple computing steps introduce a higher probability for errors in case of malfunction or failure of one or more of these sensing devices. All of these aspects complicate the design, implementation, and maintenance of a moisture sensor dedicated to routine real-time measurements of moisture content. The use of temperature- and density-insensitive calibration methods is more attractive technically and economically. This approach simplifies considerably the design, calibration, and maintenance of a moisture-sensing instrument. There have been no calibration methods that eliminate both the temperature and the density effect. Temperature can be measured with relatively inexpensive devices and its effect compensated for in the output of the sensor. However, bulk density is more troublesome, and its determination may require costly devices, particularly those designed for on-line applications. For these reasons, more academic and engineering efforts have been devoted to solving the bulk density fluctuation problem. As a result, a few density-independent calibration functions were proposed (Kraszewski et al., Journal of Microwave Power, Volume 12 (3), 241–252, 1977; Meyer and Schilz, IEEE Trans. Microwave Theory tech., Volume MTT-29 (7), 732–739, 1981; Kent and Kress-Rogers, Trans. Inst. M C, Volume 8, 161–168, 1986; Kupfer, In: Microwave Aquametry, Ed.: A. W. Kraszewski, Chapter 21, 313–327, New York, IEEE Press Book Series, 1996; and Menke et al., IEEE MTT-S International Microwave Symp. Digest, Volume 3, 1415–1418, 1996) and some were successfully used in the development of microwave moisture sensors (Nyfors and Vainikainen, 1989, supra; Kraszewski, 1996; supra; Baltes et al., 2000, supra). Though moisture content is determined independent of density, these calibration functions are either instrument-specific (Kraszewski, 1977, supra; Menke et al., 1996, supra) or require an individual calibration for each type of particulate and granular material (Kraszewski, 1977, supra; Meyer and Schilz, 1981, supra; Kent and Kress-Rogers, 1986, supra; Menke et al., 1996, supra). Therefore, there remains a need in the art for a universal calibration method that remains valid for different particulate and granular materials and that is transferable across instruments. The present invention provides a calibration method and apparatus which are different from the prior art and solves most of the limitations cited above.

The present invention is a dielectric-based calibration method that is density- and material-independent and that remains valid across instruments of different designs. It consists of a universal calibration method and apparatus that provide moisture content from a single moisture calibration equation, with temperature compensation, established from measurements at a single frequency of the dielectric properties of particulate and granular materials presenting significant structural (shape, dimensions, and surface characteristics) and compositional differences.

SUMMARY OF THE INVENTION

It is therefore an object of the present invention to provide a method and apparatus for determining moisture content in any particulate or granular material at any radio-frequency and temperature without knowledge of bulk density from a single moisture calibration equation.

A further object of the present invention is to provide a method and apparatus for determining moisture content in any particulate or granular material using a universal calibration algorithm that remains valid across instruments of different design.

Further objects and advantages of the invention will become apparent from the following detailed description.

DETAILED DESCRIPTION OF THE INVENTION

Figure 1:
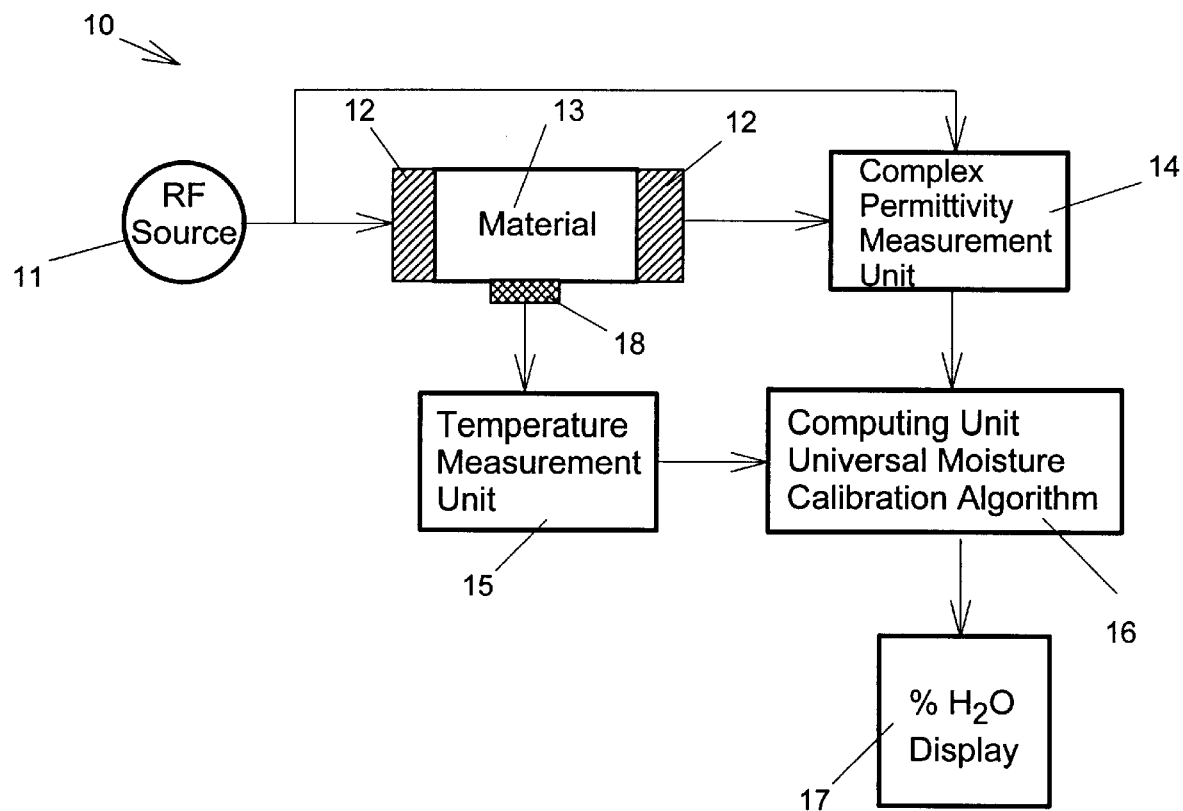
FIG. 1 is a drawing of a radio-frequency sensor for universal sensing of moisture content in particulate or granular materials.

Dielectric methods are commonly used for rapid nondestructive measurement of moisture content in cereal grain and seed, other agricultural products, and the food, lumber, chemical, pharmaceutical, concrete, and construction industries. The essence of dielectric methods is based on the electric field-material interaction which is characterized by the dielectric properties (relative complex permittivity). These properties are highly correlated to the moisture content of the material. The dielectric methods are useful because the electric field used by the moisture sensing instruments penetrates materials well, providing a volumetric sensing.

Calibration of a measuring system for indirect determination of moisture content is probably the most critical phase in the implementation of a system for routine moisture measurement, since it reflects the validity of a measurement technique and the accuracy and repeatability of the measurements. The calibration equation correlates the measured entity to the target variable such as moisture content. Usually the calibration equation involves correction and/or compensation factors to account for effects of other variables on the measured entity. Therefore, accurate determination of the different constants and correction or compensation factors involved in the calibration equation is essential. Most existing moisture sensors require temperature and bulk density compensation for particulate or granular materials. In addition, an individual calibration equation is required for each material, which complicates the calibration procedure and to some extent the design of the sensor itself. For purposes of stability and reproducibility, better performance is obtained when the number of correction and/or compensation factors in the calibration equation is minimized. Ideally, a single calibration equation involving only intrinsic properties of the material, i.e., the relative complex permittivity or a function of the relative complex permittivity, should be established for moisture determination in different materials. Accordingly, the present invention is directed to a universal dielectric-based calibration method, expressed in terms of dielectric properties, that is both density-independent and material-independent.

Particulate and granular wet materials are heterogenous mixtures of components exhibiting different dielectric behaviors. Therefore, a rigorous theoretical analysis of the wave-material interaction leading to explicit relations between the relative complex permittivity ($\epsilon=\epsilon'-j\epsilon''$) and the physical properties of the mixture is difficult to comprehend. However, because of its intrinsic character, the relative complex permittivity remains the most meaningful entity that can be used to extract other physical properties. Thus, at a given frequency (F), physical properties such as moisture content (M), bulk density ($\rho$), and temperature (T) can be determined from measurement of the relative complex permittivity. Another major advantage, if appropriate correlations between $\epsilon$, or expressions that are a function of $\epsilon$, and M, $\rho$, and T are identified, is their use regardless of the technique used for measuring the relative complex permittivity, which gives more flexibility in the design of the best sensing device for a given application.

The relative complex permittivity is measured by any radio-frequency technique which provides reliable values for the dielectric constant and the dielectric loss factor at a frequency of interest. Measurement System 10 (see FIG. 1) includes a radio-frequency source 11 for providing energy for the excitation of sensing elements 12, which can be, any of the following: transmission line, for example, cylindrical waveguide, coaxial, microstrip, free-space, antennas; electrodes; or any resonant structure. The material 13 to be measured is usually placed, or passed between or through or in close proximity to the sensing elements 12, and a signal, which depends on the radio-frequency properties of material 13, is detected by measuring unit 14 which has the capability for vectorial measurement (modulus and argument, or real and imaginary parts of a given entity), such as for example, complex impedance, complex admittance, complex reflection coefficient, complex transmission coefficient, complex angular frequency and quality factor, etc. The relative complex permittivity is computed from one or more of these measured entities. The temperature of the material 13 can be measured with a contact or noncontact temperature measuring unit 15. The relative complex permittivity output from the permittivity measuring unit 14 and temperature output from the temperature measuring unit 15 are used as inputs to a programmable computing unit 16 where data are stored and analyzed. Also, the automated measurement sequences and the universal moisture calibration algorithm are programmed into the computing unit 16. The moisture content is computed for any particulate or granular material from a single moisture calibration equation, optionally with temperature compensation, and displayed by the display unit 17 or output for use by control systems or for other use.

Figure 2:
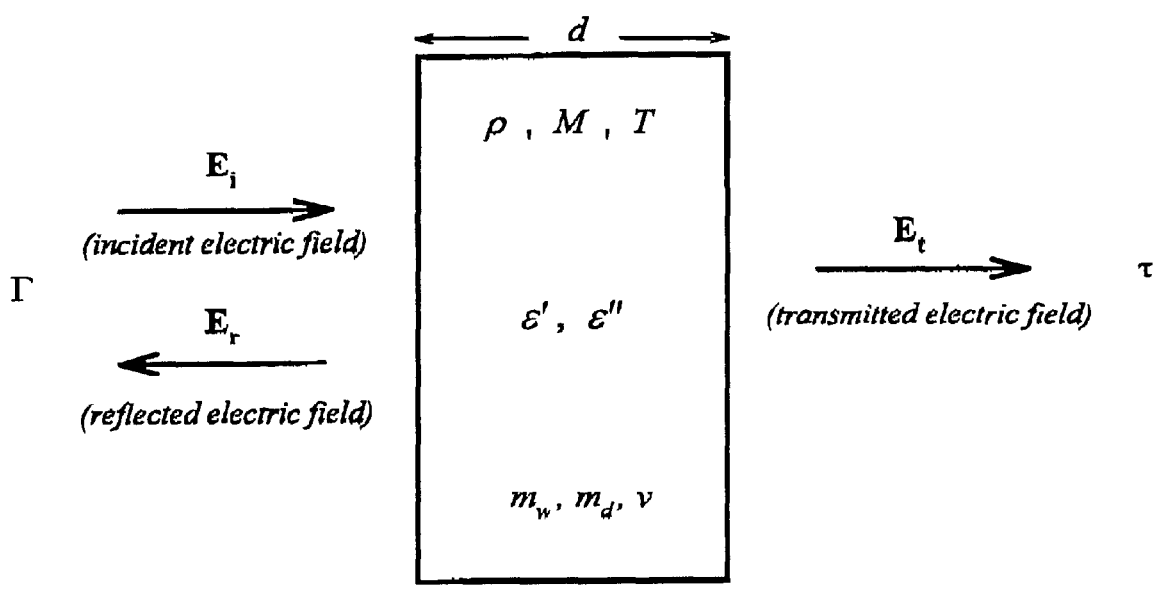
FIG. 2 is a general schematic diagram for the electric field and dielectric material interaction.

For purposes of describing the different parameters involved, such as for example, a microwave measuring system, only the reflection/transmission configuration is considered here (FIG. 2). Consider a container of thickness d and volume V filled with a nonmagnetic particulate material of moisture content M and temperature T. The moisture content in percent is defined as $$M = \frac{m_w}{m_w + m_d} \times 100 \quad (1)$$

and the bulk density is defined as $$\rho = \frac{m_w + m_d}{v} \quad (2)$$

where $m_w$ is the mass of water, and $m_d$ is the mass of dry matter of the sample making up the total mass.

For a given volume v, the mass of water and mass of dry matter can be determined if desired by combining equations (1) and (2). Moisture content is conventionally determined by oven drying techniques under well defined conditions (ASAE Standards 1999, ASAE S352.2, Moisture Measurement-unground grain and seeds, American Society of Agricultural Engineers, St. Joseph, Mich., 1999). Temperature is usually measured with thermometer or thermocouple, or thermistor devices.

All three variables, $\rho$, M, and T have similar effects on the relative complex permittivity (Trabelsi et al., Trans. ASAE, Volume 42(2), 531–536, 1999; Nelson, Cereal Chemistry, Volume 58(6), 487–492, 1981). In cereal grain and seed, the relative complex permittivity increases when $\rho$, M, or T increase. The remaining two physical properties of interest, structural and compositional, are known to effect the scattering and absorption properties of a given material but no quantitative data are available.

The essence of the definition of a density-independent and material-independent calibration function is based on elimination of interfering effects and its exclusive dependence on water content. The principle of energy distribution in dielectric materials between stored and dissipated energies and observations in the $\in'$-$\in''$ complex plane were used to define such a calibration function (Trabelsi et al., IEEE Trans. Instrum. Meas., Volume 47(3), 613–622, 1998; Trabelsi et al., U.S. Pat. No. 6,147,503, issued Nov. 11, 2000, herein incorporated by reference). Analytically, this calibration function $\psi$ is fully expressed in terms of the two components of the relative complex permittivity of the material as follows:

$$\psi = \sqrt{\frac{\varepsilon''}{\varepsilon'(a_f \varepsilon' - \varepsilon'')}} \quad (3)$$

where $\in'$ is the dielectric constant, $\in''$ is the dielectric loss factor, and $a_f$ is an empirically determined coefficient that is a function of frequency alone. The two components of the relative complex permittivity, $\in'$ and $\in''$, of a given material can be determined by any permittivity measurement technique. Measurement techniques include but are not limited to radio-frequency premittivity measurement techniques such as free-space or waveguide transmission or reflection measurements, resonant cavities or circuits and other resonant measurement structures (Nyfors and Vainikainen; supra); and electrical impedance measurements. The determination of the measurement technique is well within the ordinary skill in the art. The coefficient $a_f$ is the slope of the straight-line obtained by plotting loss factor, $\in''$, divided by bulk density, $\rho$, $\in''/\rho$, versus dielectric constant $\in'$, divided by bulk density $\rho$, $\in'/\rho$ for material samples over a range of moisture contents at a given frequency and a given temperature (or temperatures) to obtain a complex-plane representation. Once data composed of relative complex permittivity are collected for different moisture levels of materials of known moisture content and bulk density and the coefficient $a_f$ is determined for each material from the complex-plane representation, plotting $\psi$ versus moisture content, M, at a given frequency and a given temperature shows that all data points fall along the same straight line. Therefore, the data can be fitted by a single equation, which can be of the form:

$$\psi = aM + b \quad (4)$$

where a is the slope of the line and b is the intercept at a given frequency and a given temperature. The moisture content M, is determined from the following single calibration equation regardless of the material:

$$M = \frac{\psi - b}{a} \quad (5).$$

Temperature changes affect the relative complex permittivity in a way similar to that of moisture content. Analytically, $\psi$ is related to moisture content and temperature of the material as follows:

$$\psi = A \cdot M + B \cdot T + C \quad (6)$$

Therefore, to compensate the effect of temperature, equation (5) is transformed into:

$$M = \frac{\psi - BT - C}{A} \quad (7)$$

where A, B, and C are regression constants to be determined and T is the temperature.

The method of the present invention for determining the moisture content in particulate or granular materials independent of bulk densities and independent of particle geometry, size, structure, and composition, includes the steps of obtaining samples of particulate or granular materials of known moisture contents and bulk densities and in a representative range of moisture contents to be determined, and determining the dielectric constant $\in'$, and the dielectric loss factor, $\in''$, at at least one radio-frequency and at at least one temperature using any radio-frequency measurement technique. The measurements are made with a range of moisture levels for the samples to be tested for moisture content. For purposes of the present invention, particulate or granular materials include but are not limited to any manufactured or natural material, such as for example cereal grain and seed, sand, etc. The next step is to plot the dielectric loss factor $\in''$ divided by the bulk density $\rho$ versus dielectric constant $\in'$ divided by bulk density $\rho$ to obtain a complex-plane representation. The slope of the straight line in the complex-plane representation for a particular material, of known moisture content and bulk density, at each frequency is determined to obtain the coefficient $a_f$. Next, the permittivity calibration function $\psi$ is computed using equation (3) above. $\psi$ is then plotted as a function of moisture content M to form a representation. The regression constants are determined from the representation for equation (4) above. Equation (4) is then solved for M to obtain equation (5) which is used to determine the moisture content of samples of unknown moisture and unknown bulk density. These steps for the purposes of the present invention form the calibration model which includes calibration function (3) used to determine moisture content of samples of materials of unknown moisture and unknown bulk density at a given frequency and temperature. For a sample of unknown moisture and unknown bulk density, the dielectric loss factor $\in''$ and dielectric constant $\in'$ are measured at a given frequency and temperature, as in the first step above, and the moisture content is determined using the calibration model and the moisture calibration equation (5). For measurements in environments with changing temperatures, equation (7) is used in place of equation (5) to compensate for temperature effects.

Hence, the instant invention allows moisture determination independent of bulk density and independent of the material at any temperature. This simplifies considerably the calibration procedure and the design of a cost-effective moisture sensor dedicated to nondestructive, instantaneous moisture content determination in bulk particulate or granular materials with pronounced differences in particle geometry, dimensions, and composition.

The following examples illustrate the use of the invention for density-independent and material-independent moisture determination of particulate or granular materials using the universal dielectric calibration method of the present invention. For these examples, a free-space transmission microwave technique is used as a model system. The examples are intended to further demonstrate the invention and are not intended to limit the scope of the invention defined by the claims.

EXAMPLE 1

Among all the techniques for dielectric materials characterization, free-space techniques are more suitable for implementation in many industrial processes. They can be used either in reflection or transmission mode or both, and thus, they can be easily adapted and installed on line for almost any configuration including conveyor, pipe, or chute. FIG. 2 shows a general schematic diagram of wave-material interaction for a layer of granular material of thickness d in free space. The reflected wave at the front interface is characterized by the reflection coefficient $\Gamma$, and the transmitted wave is characterized by the transmission coefficient $\tau$.

In free space, accuracy of the relative complex permittivity measurements is related to a combination of factors. The most significant errors are related to near-field effects, scattering, diffraction at the edges of the sample, multiple reflections within the sample and between the different components for the measuring system, and interference with surrounding objects. Therefore, particular attention must be paid to the choice of frequency or frequency range, the sample size, distances between antennas and the sample, and, in some instances, distances from surroundings.

For example, measurement system 20 (FIG. 3) can consist of transmitter 22a and receiver 22b of antennas 22, about 1 to 21 GHz, connected with high quality coaxial cables to an S-parameter test set 23 of a computing unit, e. g.,vector network analyzer (VNA) 24 (Hewlett-Packard 8510B for example). The VNA is calibrated in the transmission mode between about 2 and 13 GHz with an empty sample holder 27 located between the antennas 22. Antennas 22 are mounted about 61 cm apart on a base 25 to keep them well aligned. The antennas 22 collimate the electromagnetic energy in a relatively small beam and provide a plane wave a short distance from the transmitting antenna 22a. With these features, the measurements are performed on samples of reasonable size without problems of edge diffraction or interference by reflections from the surroundings. The sample is presented to the incident electric field in the form of a layer of appropriate dimensions and placed midway between the transmitting 22a and receiving 22b antennas 22.

For each sample 26, the material is poured into a sample holder 27, made of approximately a 2.5-cm-thick Styrofoam sheet ($\in$=1.03) with a rectangular cross section. The dimensions of the layer are about 25 cm transverse, about 25 cm in height, and about 10.9, 15.3, and 11.1 cm in thickness. The transverse and height dimensions are selected to minimize the diffraction effects at the edges of sample 26 by fulfilling the criterion of three times the E-plane 3-dB beamwidth over the whole frequency range (Ghodgaonkar et al., IEEE Trans. Instrum. Meas., Volume 39(2), 387–394, 1990). To avoid multiple reflections within the sample, for each material the thickness is selected to ensure a 10-dB one-way attenuation through the sample 26. In general, the selection of sample 26 thickness is a compromise among minimizing multiple reflections, reducing scattering effects, and optimum use of the dynamic range of the measuring system. To eliminate residual post-calibration reflections and possible multiple transmission paths, an appropriate time-domain gating is applied so that the gated frequency-domain response is a good average of the ungated response.

Post-calibration mismatches and multiple transmission paths cause oscilloscope traces observed in the frequency domain, in this instance the magnitude and phase of the scattering transmission coefficient, to exhibit ripples with variable magnitudes. This will translate into errors in the permittivity measurements. To remove such effects, the frequency-domain trace is converted to the time domain. After identifying the main response, a gate is applied to filter out the unwanted responses. Then, the gated response is converted back to the frequency domain. The trace was then ripple free, indicating that the effects of responses outside the gate were removed. Effectiveness of time-domain gating relies mainly on appropriate selection of the gate parameters. For each material, these parameters are selected after several trials on different samples for which the gated frequency-domain response is a good average of the ungated response.

Figure 4:
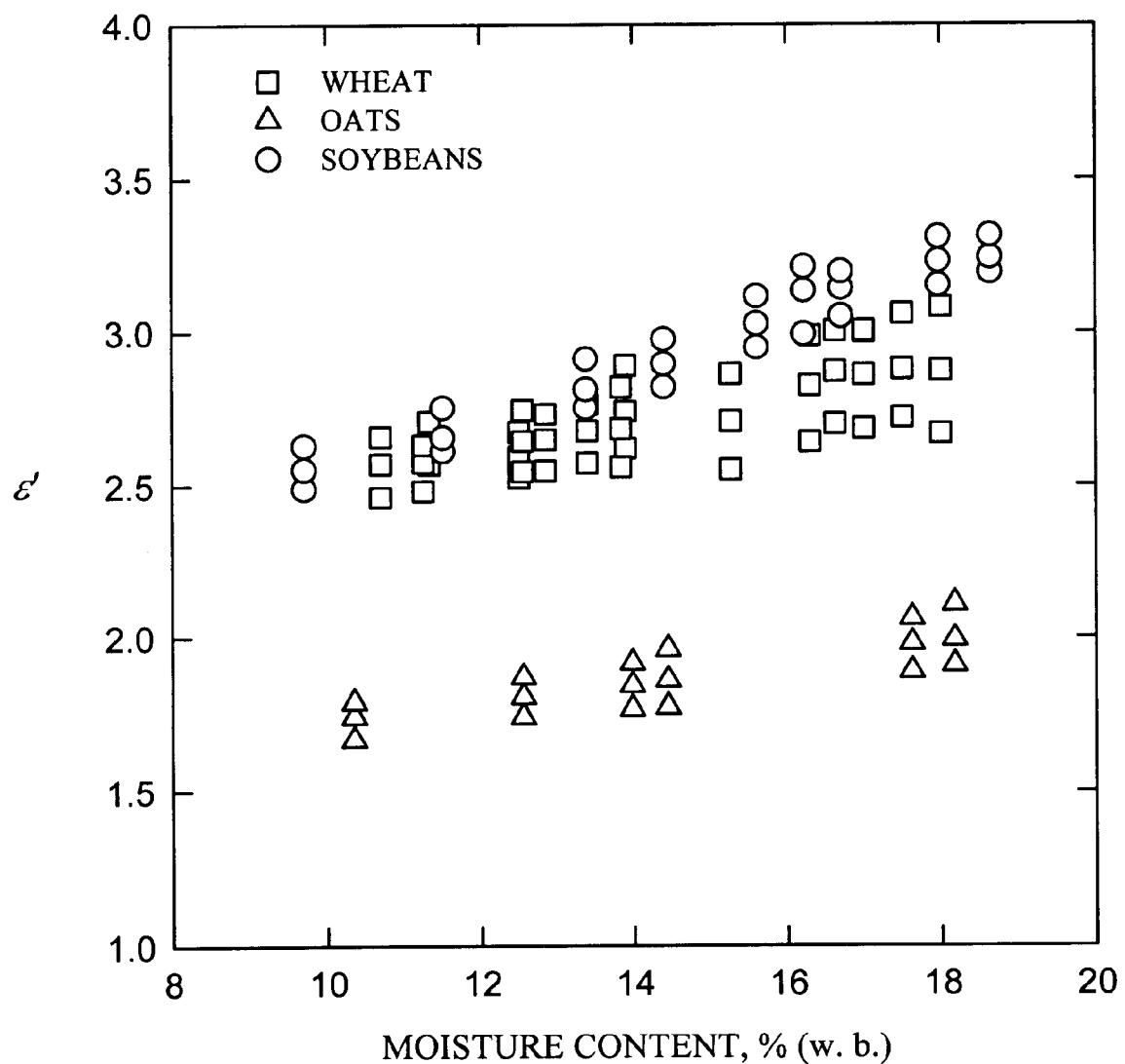
FIG. 4 is a graph showing the moisture dependence of the dielectric constant, $\epsilon'$, for samples of wheat, oats, and soybeans of different bulk densities at about 9.46 GHz and 24° C.
Figure 5:
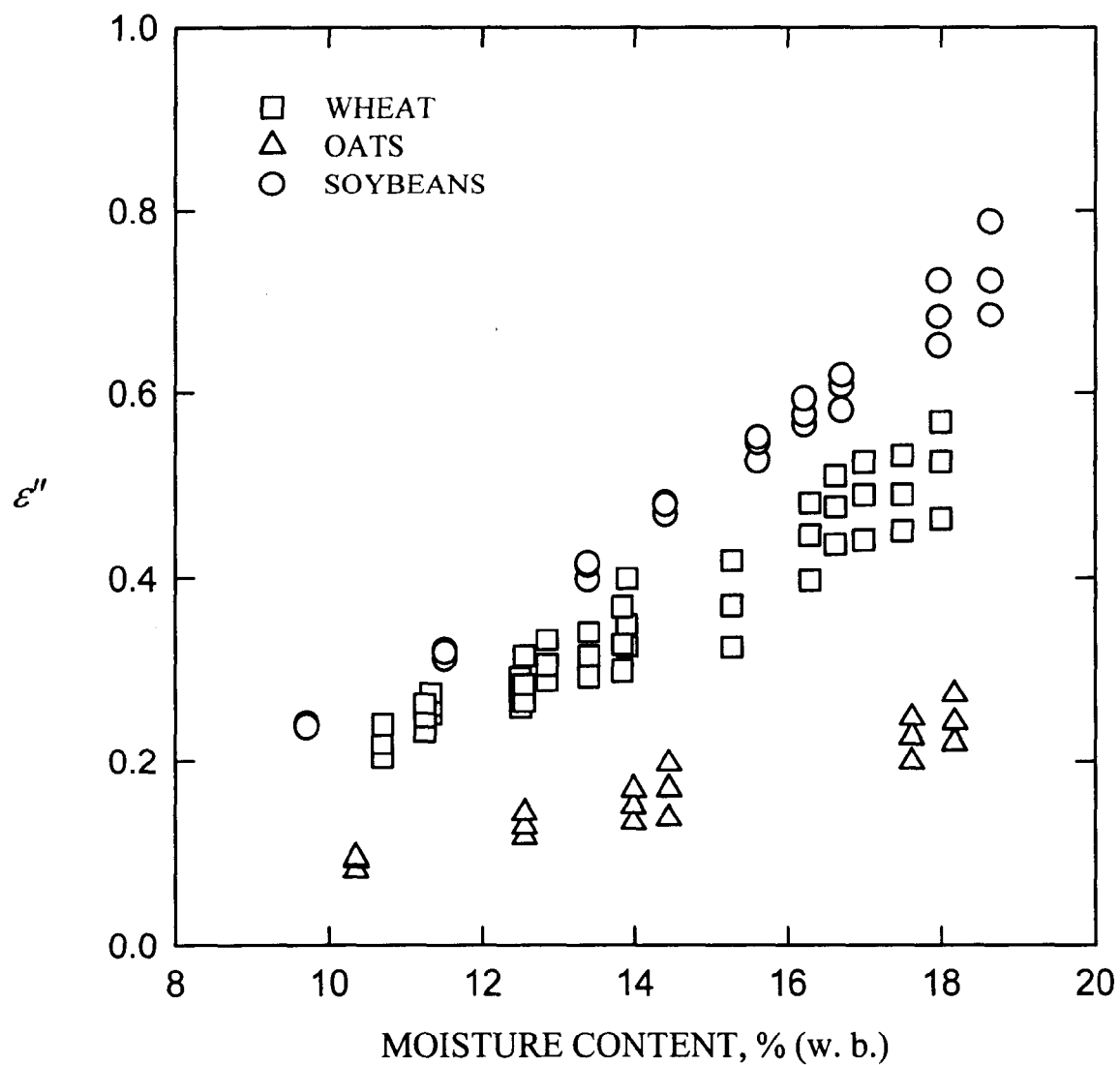
FIG. 5 is a graph showing the moisture dependence of loss factor, $\epsilon''$, for samples of wheat, oats, and soybeans of different bulk densities at about 9.46 GHz and 24° C.

To test the density-independent and material-independent character of the calibration function ψ, materials with significant structural and compositional differences were used, i.e., wheat, oats, and soybeans (Table 1). The samples were presented to the incident electromagnetic wave in a sample holder, as described above and placed between the two antennas 22 (See FIG. 3). The dimensions of the layer were about 25 cm transverse, about 25 cm in height and of thickness as indicated in Table 1 below. The transverse and height dimensions were selected as described above in the detailed description. From measurements of the attenuation A and the phase shift Φ introduced by a sample of thickness d, the dielectric constant and loss factor were calculated according to:

$$\varepsilon' = \left(\frac{\beta}{\beta_0}\right)^2 \tag{8}$$

$$\varepsilon'' = \frac{2\alpha\beta}{\beta_0^2} \tag{9}$$

where $\alpha = A/d$ is the attenuation constant, $\beta = \Phi/d + \beta_0$ is the phase constant, and $\beta_0 = 2\pi/\lambda_0$ is the phase constant for free-space wavelength $\lambda_0$. FIGS. 4 and 5 show variations of ∈' and ∈" for samples of wheat, oats, and soybeans of different bulk densities with moisture content at 9.4 GHz and room temperature (about 24°C.). Although, at microwave frequencies, water is expected to dominate the wave-material interaction, variations of ∈' and ∈" with moisture content suggest that they are affected by other entities. The effect of bulk density is obvious for both materials, with the dielectric properties of soybeans presenting, in general, higher values and greater slope than those of wheat and oats. In this form, the data cannot be used for moisture content prediction without compensation for the density effect for each material.

Density determination often involves additional devices and complicates somewhat the calibration procedures and the design of the moisture sensor. A better alternative is the use of the concept of moisture sensing independent of bulk density fluctuations.

Figure 6:
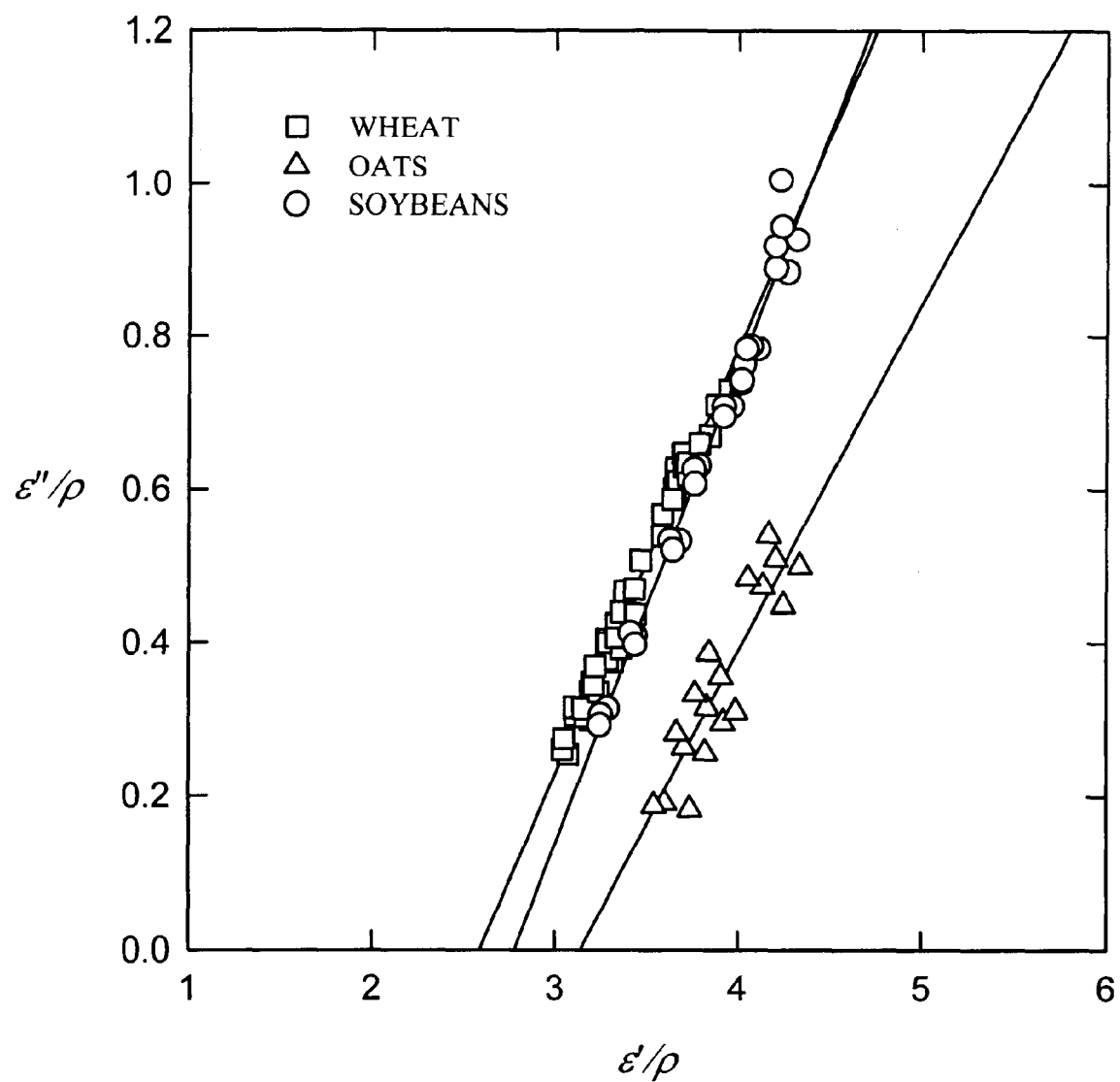
FIG. 6 is an Argand diagram of the relative complex permittivity divided by bulk density for wheat, oats, and soybeans at about 9.46 GHz and 24° C.

The density-independent character of the calibration function ψ is well established as was reported elsewhere (Trabelsi et al., IEEE Trans. Instrum. Meas., Volume 47 (3), 613–622, 1998; Trabelsi and Nelson, Meas. Sci. Techn., Volume 9(4), 570–578, 1998; and Trabelsi et al., Trans. ASAE, Volume 42(2), 531–536, 1999). To compute ψ, values of ∈', ∈" and $a_f$ are needed. The dielectric properties, ∈' and ∈", are determined, for example, from measurement of attenuation A and phase shift Φ. The coefficient $a_f$ is determined from the complex-plane representation of the relative complex permittivity divided by density as shown in FIG. 6. For each material, the data points fall along a straight line which can be fitted by linear regression as follows:

$$\frac{\varepsilon''_{wheat}}{\rho} = 0.555 \frac{\varepsilon'_{wheat}}{\rho} - 1.436 \quad r^2 = 0.98 \tag{10}$$

$$\frac{\varepsilon''_{oat}}{\rho} = 0.452 \frac{\varepsilon'_{oat}}{\rho} - 1.42 \quad r^2 = 0.81 \tag{11}$$

$$\frac{\varepsilon''_{soy}}{\rho} = 0.619 \frac{\varepsilon'_{soy}}{\rho} - 1.72 \quad r^2 = 0.98 \tag{12}$$

The slope of each straight line is $a_f$, 0.555 for wheat, 0.452 for oats, and 0.6189 for soybeans, respectively. Equations (10), (11), and (12) can be used to determine bulk density from dielectric properties measurements without knowing temperature and moisture content.

Figure 7:
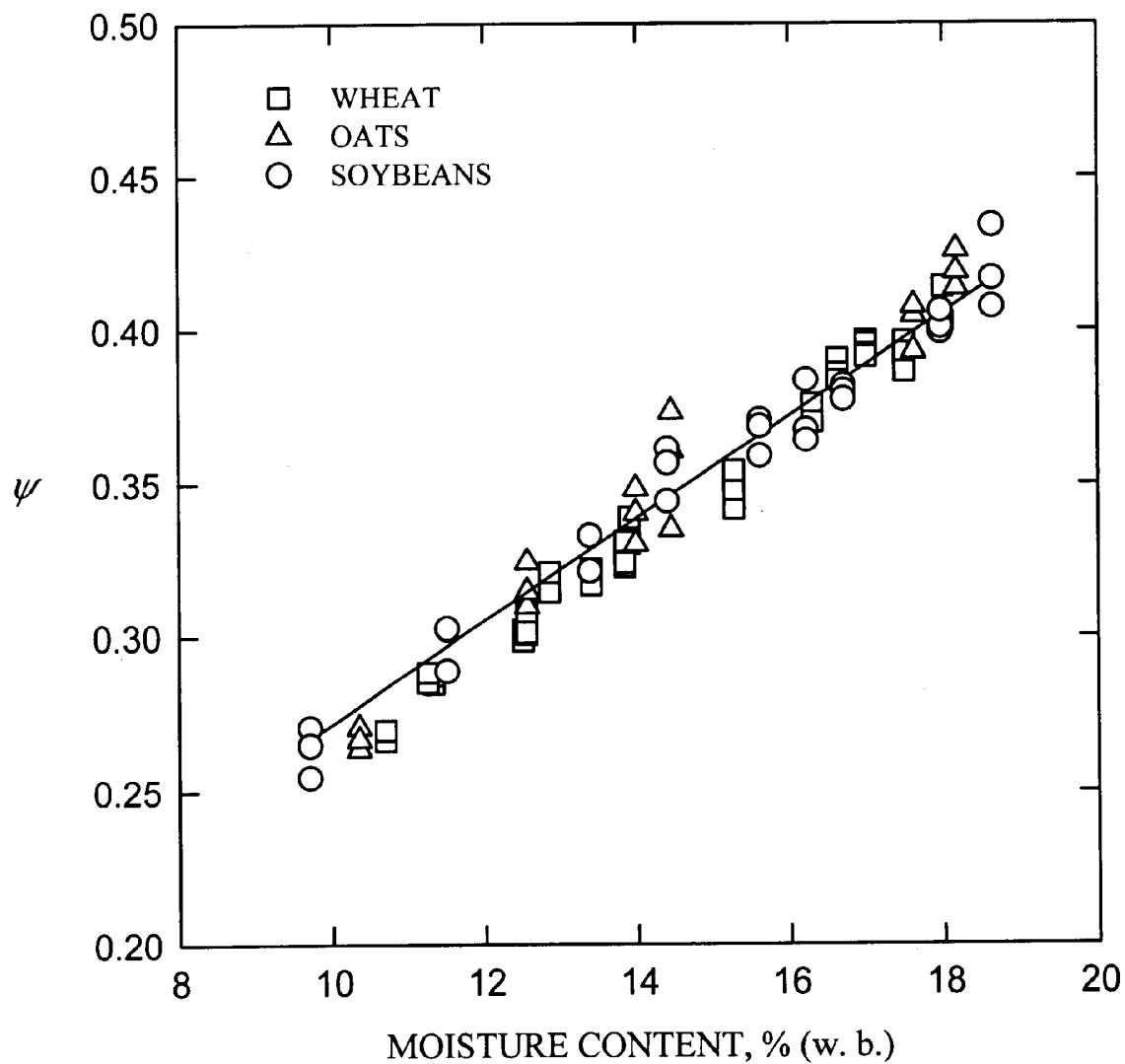
FIG. 7 is a graph showing dependence of universal calibration function $\psi$ on moisture content in wheat, oats, and soybeans at about 9.46 GHz and 24° C.

Variations of the calibration function ψ with moisture content are plotted for each material at 9.46 GHz and room temperature as shown in FIG. 7. ψ increases linearly with moisture content with all data points corresponding to wheat, oats, and soybeans superimposed. Therefore, the combined data (wheat, oats, and soybeans) can be fitted by a single linear regression as follows:

$$\psi = 0.018 \cdot M + 0.083 \quad r^2 = 0.97 \tag{13}$$

From equation (13), a single moisture calibration equation for moisture content computation is obtained:

$$M = 55.55 \cdot \psi - 4.61 \tag{14}$$

Therefore, a single calibration equation is sufficient to determine moisture content in wheat, oats, and soybeans from measurements of their respective dielectric properties, making this calibration function both density-independent and material-independent. The standard error of calibration (SEC), when using equation (14) to predict moisture content in wheat, oats, and soybeans, was about 0.46% moisture content, wet basis.

EXAMPLE 2

Figure 3:
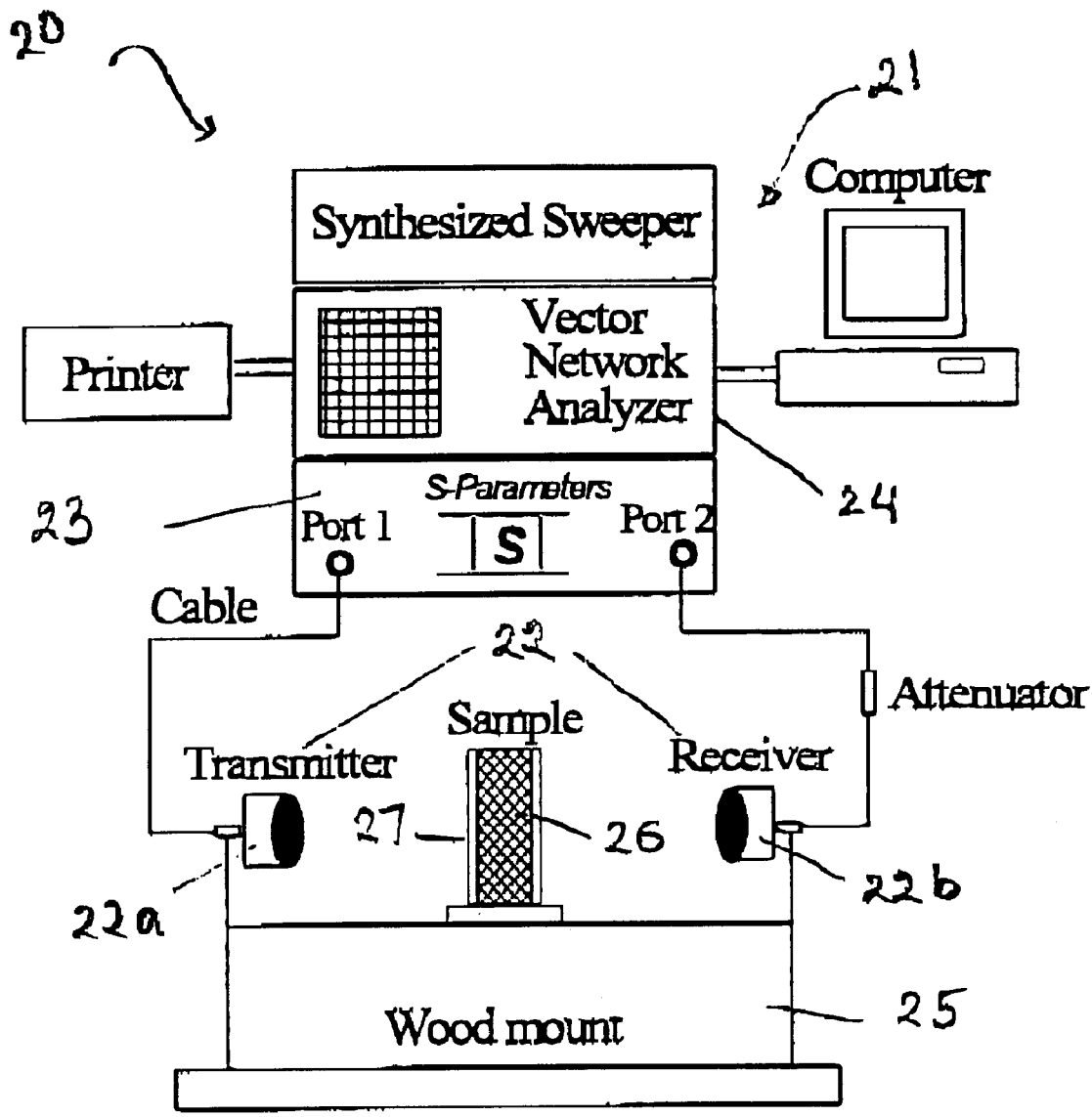
FIG. 3 is a drawing of a free-space transmission measurement system.

This example illustrates the universal character of the calibration method and the transferability of the universal algorithm through measurement of the dielectric properties with different measurement arrangements. Moisture calibration equations with temperature compensation are given for wheat, corn and soybeans, three materials with pronounced differences in geometry, dimensions, and composition. Two free-space measurement arrangements were used for the characterization of these materials. In the first arrangement, samples of wheat and corn were poured into a Styrofoam container which was then placed between two WR-62 horn antennas connected to a vector network analyzer (Hewlett-Packard 8510B) through waveguide-to-coaxial adaptors and high quality coaxial cables (FIG. 3). For each material, the sample holder filled with the kernels was positioned in the near field with the front and back interfaces very close to the antenna apertures. Measurements were performed at microwave frequencies over wide ranges of bulk density, moisture content, and temperature (Table 2 below).

Figure 8:
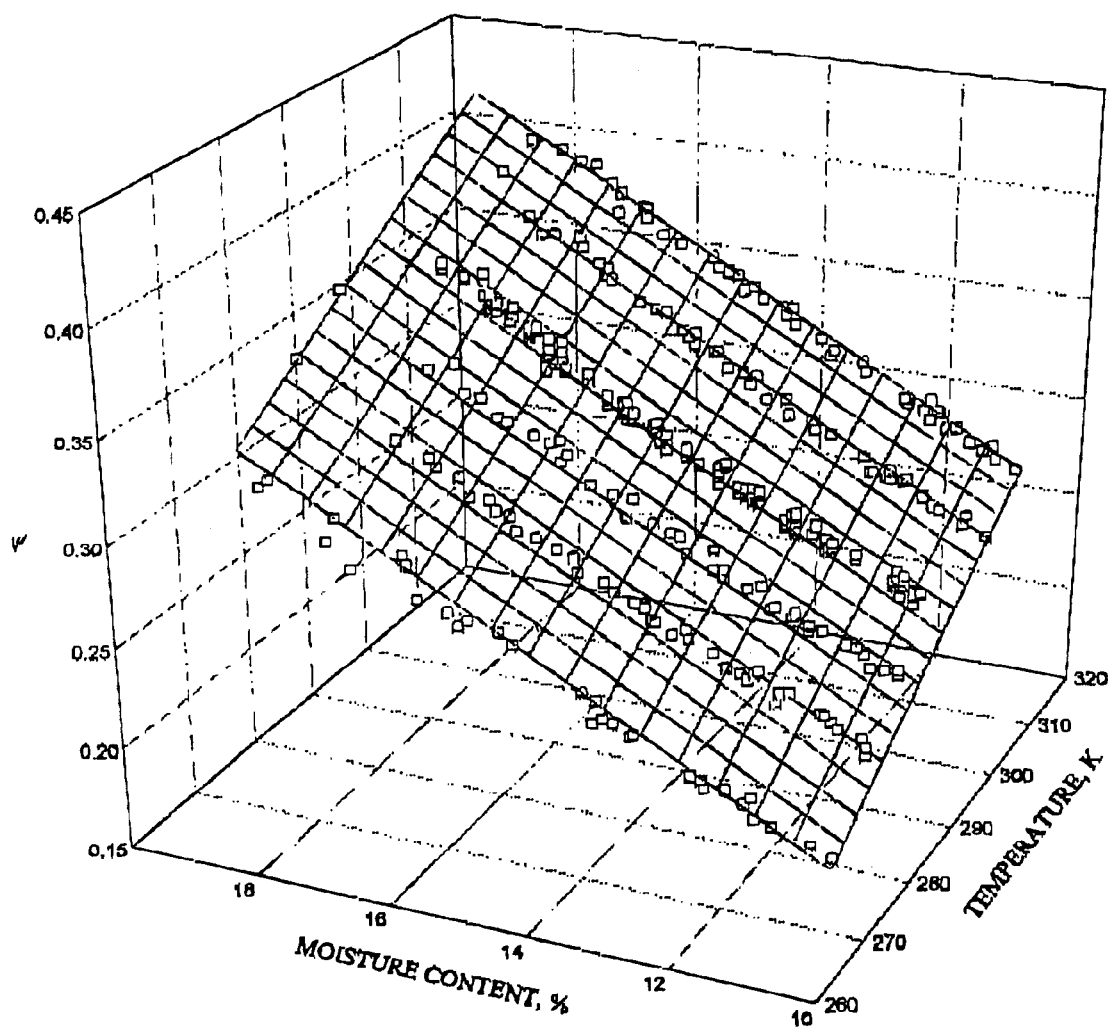
FIG. 8 is a graph showing moisture and temperature dependence of calibration function $\psi$ at about 14.2 GHz for wheat.
Figure 9:
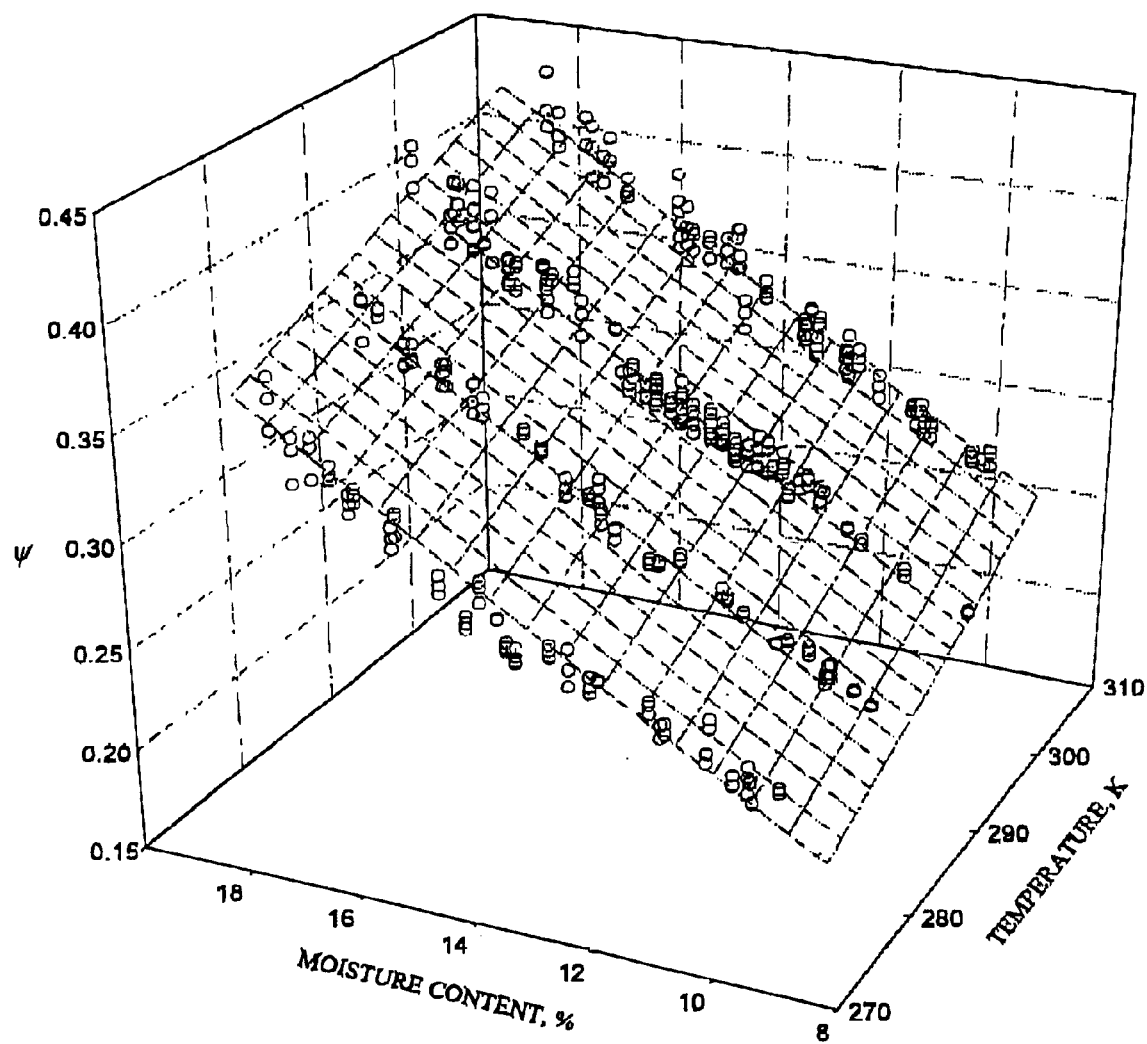
FIG. 9 is a graph showing moisture and temperature dependence of calibration function $\psi$ at about 14.2 GHz for corn.
Figure 10:
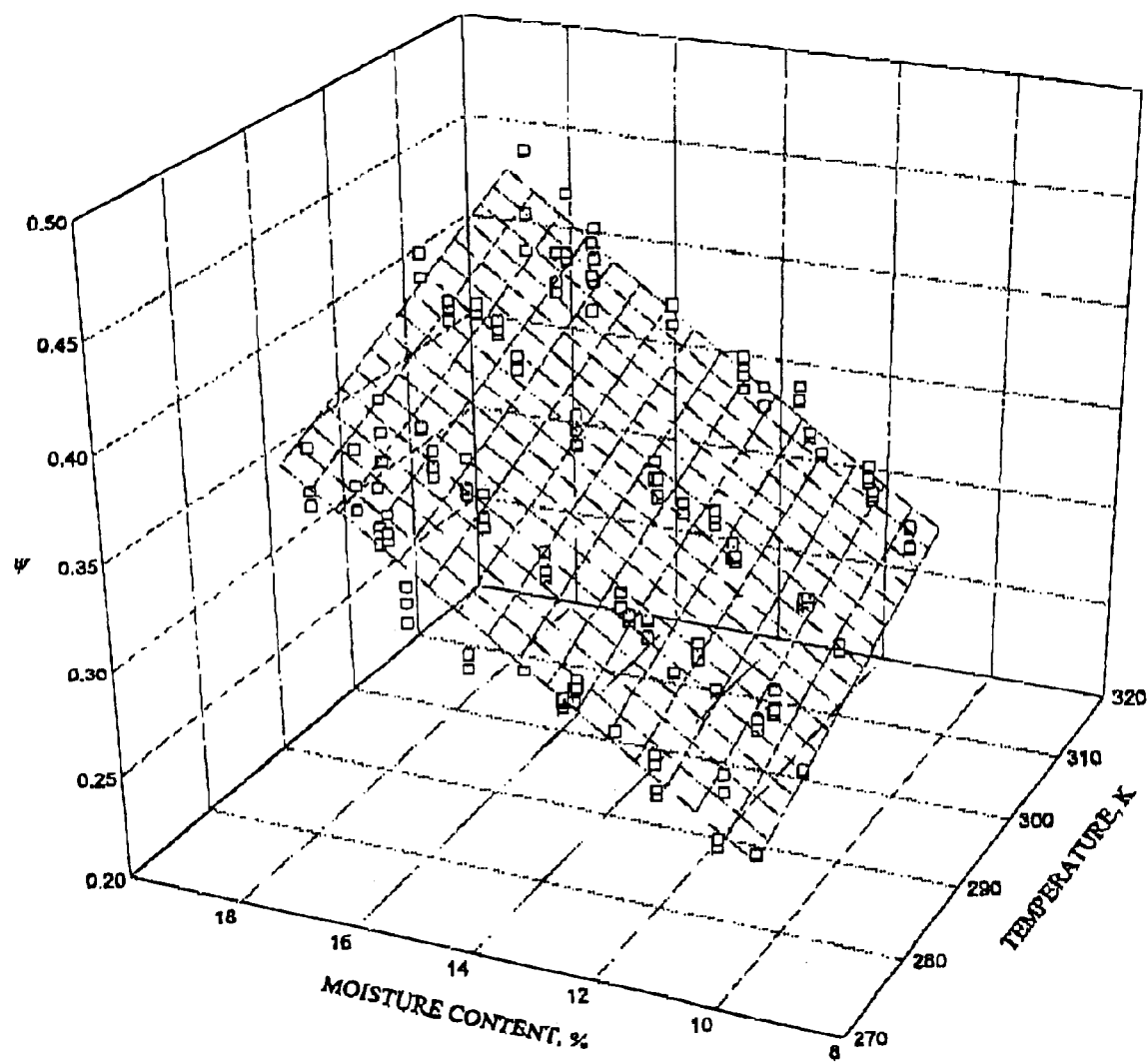
FIG. 10 is a graph showing moisurre and temperature dependence of calibration function $\psi$ at about 9.46 GHz for wheat.

FIGS. 8 and 9 show variation of the calibration function ψ as a function of temperature and moisture content at about 14.2 GHz for wheat and corn, respectively. These three-dimensional representations reveal that data points for each material lie in the same plane, forming a network of nearly parallel straight lines. A regression analysis provides the equation of the plane for each material:

$$\psi_{wheat} = 0.0174 \cdot M + 0.0022 \cdot T - 0.62 \quad r^2 = 0.99 \tag{15}$$

$$\psi_{corn} = 0.0166 \cdot M + 0.0023 \cdot T - 0.59 \quad r^2 = 0.97 \tag{16}$$

Although wheat and corn kernels have significant differences in shape, dimensions, and composition, the coefficients of the fitting equations are very similar, implying that a single equation can be used to correlate the calibration function with M and T. Combining wheat and corn data in one data set, the regression analysis provides one equation for both materials:

$$\psi = 0.0167 \cdot M + 0.0021 \cdot T - 0.574 r^2 = 0.935 \quad (17)$$

Solving for M, a single moisture calibration equation with temperature compensation is obtained:

$$M = 59.73 \cdot \psi - 0.126 \cdot T + 34.29 \quad (18)$$

Figure 11:
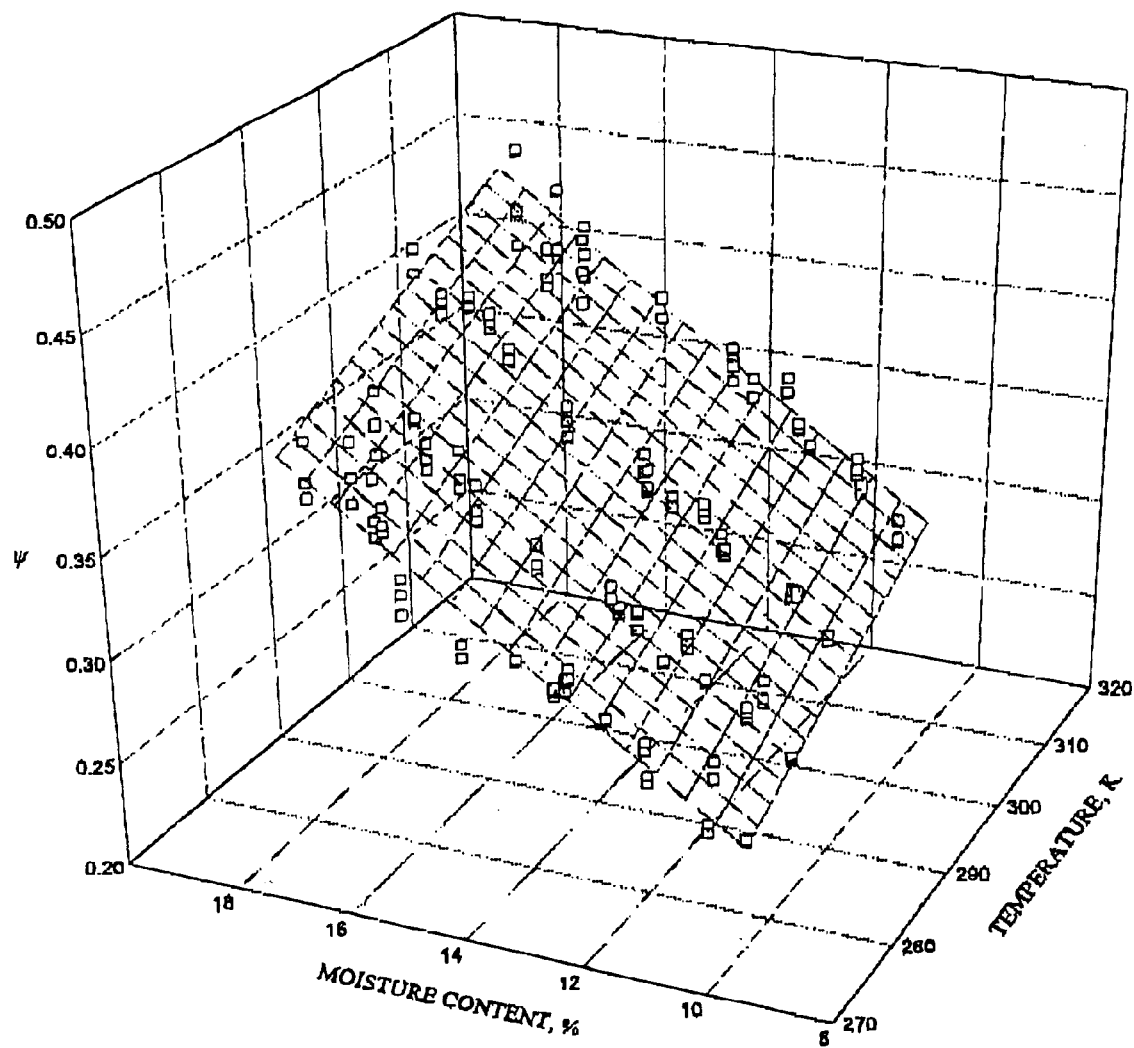
FIG. 11 is a graph showing moisture and temperature dependence of calibration functions $\psi$ at about 9.46 GHz for soybeans.

For Far-field permittivity measurements, samples of wheat and soybeans, each in separate measurements, were poured into a Styrofoam container which was placed midway between two horn/lens antennas, BAE SYSTEMS, model AHO-2077-N, connected to the vector network analyzer. The antennas were about 61 cm apart. The antennas provided a narrow beam at short distances from the transmitter and thus a plane wave was propagating between the two antennas and through the sample. To improve the measurement accuracy, time-domain gating was applied to the main response to filter out effects of post-calibration mismatches and possible multiple transmission paths. Measurements were performed at microwave frequencies over wide ranges of bulk density, moisture content, and temperature (Table 3 below). FIGS. 11 and 12 show the calibration function $\psi$ as a function of temperature and moisture content at 9.46 GHz for wheat and soybeans, respectively. In the same way as for wheat and corn, these three-dimensional representations reveal that data points obtained for each material lie in the same plane, forming a network of nearly parallel straight lines. A regression analysis provided the equation of the plane for each material:

$$\psi_{wheat} = 0.0185 \cdot M + 0.002 \cdot T - 0.51 r^2 = 0.95 \quad (19)$$

$$\psi_{soybeans} = 0.0164 \cdot M + 0.0022 \cdot T - 0.56 r^2 = 0.98 \quad (20)$$

Although wheat and soybean kernels have significant structural and compositional differences, the coefficients of the fitting equations are very similar, implying that a single equation can be used to correlate the calibration function with M and T. Combining wheat and soybean data in one data set, the regression analysis provides one equation for both materials:

$$\psi = 0.017 \cdot M + 0.0023 \cdot T - 0.587 r^2 = 0.94 \quad (21)$$

Solving for M, a single moisture calibration equation with temperature compensation is obtained:

$$M = 58.48 \cdot \psi - 0.134 \cdot T + 34.32 \quad (22)$$

Moisture equations (18) and (22) are very similar although they were obtained for different materials with two different free-space measurement arrangements.

This example shows that the universal calibration method provides a single moisture calibration equation for materials with significant structural and compositional differences over wide temperature and bulk density ranges. In industrial environments, this will provide a stable calibration procedure that tolerates temperature and density changes. Furthermore, measurements in the near field with two basic horn antennas are similar to those obtained in the far field with sophisticated horn/lens antennas with time-domain gating. This demonstrates the universal nature of the method in that it is not dependent on the measurement system. In industrial situations, the universal calibration will remain valid across instruments of different designs. Also, when space is a critical factor, along with other mechanical constraints, the sensor can be confined in a relatively small space.

TABLE 1

Characteristics of grain and seed samples

| Material | Sample Thickness, cm | Density range, g/cm³ | Moisture content range, % | Kernel length, mm | Shape |
|---|---|---|---|---|---|
| Wheat | 10.9 | 0.69–0.87 | 10.7–18.0 | 5–7 | ellipsoidal |
| Oats | 15.3 | 0.44–0.51 | 10.3–18.2 | 8–12 | ellipsoidal |
| Soybeans | 11.1 | 0.73–0.81 | 9.7–18.6 | 5–7 | spherical |

TABLE 2

Characteristics of wheat and corn samples.

| Material | Sample Thickness, cm | Bulk density range, g/cm³ | Moisture Content Range, % w.b. | Temperature range, K | Kernel length, mm | Shape |
|---|---|---|---|---|---|---|
| Wheat | 10.4 | 0.72–0.88 | 10.6–19.2 | 272–318 | 5–7 | ellipsoidal |
| Corn | 5.2 | 0.69–0.83 | 9–19.2 | 277–308 | 12–13 | oblate |

TABLE 3

Characteristics of Wheat and Soybean samples

| Material | Sample Thickness, cm | Density range, g/cm³ | Moisture Content Range, % w.b. | Temperature range, K | Kernel length, mm | Shape |
|---|---|---|---|---|---|---|
| Wheat | 10.9 | 0.69–0.8 | 10.4–18.0 | 278–309 | 5–7 | ellipsoidal |
| Soybeans | 11.1 | 0.73–0.82 | 19.7–18.7 | 262–311 | 12–13 | spherical |

The foregoing detailed description is for the purpose of illustration. Such detail is solely for that purpose and those skilled in the art can make variations therein without departing from the spirit and scope of the invention.

| INDEX OF THE ELEMENTS | |
|---|---|
| 10. | Measurement System |
| 11. | Radio-Frequency Source |
| 12. | Sensing Elements |
| 13. | Material |
| 14. | Permittivity Measuring Unit |
| 15. | Temperature Measuring Unit |
| 16. | Programmable Computer Unit |
| 17. | Display Unit |
| 20. | Measurement System |
| 22. | Antennas |
| 22a. | Transmitter |
| 22b. | Receiver |
| 23. | S-Parameter Test Set |
| 24. | Vector Network Analyzer |
| 25. | Base |
| 26. | Sample |
| 27. | Sample Holder |

We claim:

1. A method for determining moisture content of materials of unknown moisture content comprising:
   1. determining a universal moisture calibration equation wherein the determination of said calibration equation comprises:
      (a) obtaining granular or particulate materials of different geometry, dimensions, and compositions, wherein said materials have known moisture contents and bulk densities and represent the range of moisture contents to be determined;
      (b) determining dielectric constant $\varepsilon'$ and dielectric loss factor $\varepsilon''$ at at least one radio-frequency and at one temperature for each of said materials,
      (c) creating a complex-plane representation by plotting $$\left(\frac{\varepsilon''}{\rho}\right)$$

versus $$\left(\frac{\varepsilon'}{\rho}\right)$$

at at least one radio frequency and at one temperature for each of said materials;
      (d) determining the slope $a_f$ for each of said material at at least one radio frequency from step 1(c);
      (e) computing for each of said materials a permittivity calibration function $\psi$ as $$\psi = \sqrt{\frac{\varepsilon''}{(\varepsilon')(a_f\varepsilon' - \varepsilon'')}} \; ;$$

(f) plotting $\psi$ versus said known moisture contents to form a graphical representation;
      (g) performing a linear regression using the graphical representation in step 1(f) using the equation $\psi=(a)$M+b in order to determine the regression constants a and b; and
      (h) defining a universal moisture calibration equation from step 1(g) as $$M = \frac{\psi - b}{a}$$

a wherein a and b are said regression constants determined in step 1(g);
   2. using the universal calibration equation of step 1(h) to determine moisture content of any particulate or granular materials of unknown moisture contents and unknown bulk densities comprising the steps of:
      (a) obtaining any particulate or granular materials having unknown moisture contents and unknown bulk densities,
      (b) determining $\varepsilon'$ and $\varepsilon''$ for each of said materials;
      (c) computing $\psi$ for said materials using said equation defined in 1(e); and
      (d) determining the moisture content for each of said materials using the universal moisture calibration equation defined in step 1(h), wherein said dielectric constant and dielectric loss factor are determined using radio-frequency permittivity measurements including transmission-line measurement techniques, resonant cavities or circuits, or other resonant structures; or electrical impedance or admittance measurement;
         wherein said method of using said universal moisture calibration is density independent and material independent.

2. An apparatus for measuring moisture content in any particulate or granular material comprising:
   (a) a radio-frequency source for generating electromagnetic waves;
   (b) at least one sensing element operatively connected at an output termination to said radio-frequency source;
   (c) a complex permittivity measurement unit operatively connected to at least one termination of said sensing element;
   (d) a programmable computing unit, operatively connected to an output of said complex permittivity measurement unit wherein said unit stores and analyzes data in order to provide moisture content of a sample;
   (e) a computer readable medium for computing moisture content of any particulate or granular material having differences in geometry, dimensions, and compositions wherein said moisture content is determined by the method of claim 1; and
   (f) a display unit operatively connected to said programmable computing unit for displaying said moisture content.

3. A method for determining moisture content of materials of unknown moisture content consisting essentially of:
   1. determining a universal moisture calibration equation wherein the determiniation of said calibration equation comprises:
      (a) obtaining granular or particulate materials of different geometry, dimensions and compositions and having known moisture contents and bulk densities which represent the range of moisture contents to be determined;
      (b) determining dielectric constant $\varepsilon'$ and dielectric loss factor $\varepsilon''$ at at least one radio frequency and at different temperatures for each of said materials;
      (c) creating a complex-plane graphical representation by plotting $$\left(\frac{\varepsilon''}{\rho}\right)$$

versus $$\left(\frac{\varepsilon'}{\rho}\right)$$

at at least one radio frequency and at different temperatures for each of said materials;
      (d) determining slope $a_f$ for each of said materials at at least one radio frequency from step 1(c);
      (e) computing for each material a permittivity calibration function $\psi$ as $$\psi = \sqrt{\frac{\varepsilon''}{(\varepsilon')(a_f\varepsilon' - \varepsilon'')}} \; ;$$

(f) plotting $\psi$ versus said known moisture contents and temperatures to form a graphical three dimensional representation which forms a plane surface;

(g) performing a regression using the graphical representation in step 1(f) using the equation $$\psi = (A)M + (B)T + C$$

in order to determine the regression constants A, B, and C; and (h) defining a universal moisture calibration equation from step 1(g) as $$M = \frac{\psi - (B)T - C}{A}$$

where A, B, and C are said regression constants determined in step 1(g);

2. using the universal moisture calibration equation of step 1(h) to determine moisture content of any particulate or granular materials of unknown moisture contents and unknown bulk densities comprising the steps of:

(a) obtaining any particulate or granular materials of unknown moisture contents and unknown bulk densities;

(b) determining $\in'$ and $\in''$ for said materials;

(c) determining temperature of said materials;

(d) computing $\psi$ for said materials using said equation defined in step 1(e); and (e) determining the moisture content of said materials using the universal calibration equation defined in step 1(h); wherein said dielectric constant and dielectric loss factor are determined using radio frequency permittivity measurements including transmission-line measurement techniques, resonant cavities, resonant circuits, or other resonant structures; or electrical impedance or admittance measurements;

wherein said method of using said universal calibration is density independent and material independent.

4. An apparatus for measuring moisture content in any particulate material comprising:

(a) a radio-frequency source for generating electromagnetic waves;

(b) at least one sensing element operatively connected at an input termination to said radio-frequency source;

(c) a complex permittivity measurement unit operatively connected to at least one termination of said sensing element;

(d) a contact or noncontact temperature measurement unit positioned in or in proximity with a particulate or granular material;

(e) a programmable computing unit, operatively connected to an output of said complex permittivity measurement unit and an output of said temperature measurement unit wherein said unit stores and analyzes data in order to provide moisture content of a sample;

(f) a computer readable medium for computing moisture content of any particulate or granular material having differences in geometry, dimensions, and compositions wherein said moisture content is determined by the method of claim 3; and (g) a display unit operatively connected to said programmable computing unit for displaying said moisture content.

\* \* \* \* \*